(12) United States Patent
Ballard et al.

(10) Patent No.: US 6,849,624 B2
(45) Date of Patent: Feb. 1, 2005

(54) AROMATIC AND HETEROAROMATIC SUBSTITUTED AMIDES

(75) Inventors: Theresa Maria Ballard, Basel (CH); Torsten Hoffmann, Weil am Rhein (DE); Sonia Maria Poli, Basel (CH); Patrick Schnider, Oberwil (CH); Andrew Sleight, Riedisheim (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 48 days.

(21) Appl. No.: 10/196,795

(22) Filed: Jul. 17, 2002

(65) Prior Publication Data

US 2003/0064983 A1 Apr. 3, 2003

(30) Foreign Application Priority Data

Jul. 31, 2001 (EP) .............................. 01118412

(51) Int. Cl.$^7$ ...................... A61K 31/54; C07D 279/10; C07D 279/12; C07D 295/00
(52) U.S. Cl. .................................. 514/227.5; 544/58.2
(58) Field of Search ...................... 514/227.5; 544/58.2

(56) References Cited

U.S. PATENT DOCUMENTS

| 5,972,938 A | 10/1999 | Rupniak et al. | |
| 2003/0004157 A1 * | 1/2003 | Buser et al. ................ | 514/217 |

FOREIGN PATENT DOCUMENTS

| EP | 1 035 115 A1 | 9/2000 |
| GB | 2 347 422 | 9/2000 |
| WO | WO 95/16679 | 6/1995 |
| WO | WO 95/18124 | 7/1995 |
| WO | WO 95/23798 | 9/1995 |
| WO | WO 02 085458 | 10/2002 |

OTHER PUBLICATIONS

Stout et al, "Neurokinin 1 Receptor Antagonists as Potential Antidepressants" Annu. Rev. Pharmacol. Toxicol. vol. 41, pp. 877–906 (2001).*

Rupniak, N. "Elucidating the antidepressant actions of substance P (NK 1 receptor) antagonists" Current Opinion in Investigational New Drugs, vol. 3(2), pp. 157–261 (2002).*
Humphrey, J. "Medicinal Chemistry of Selective Neurokinin–1 Antagonists" Current Topics in Medicinal Chemistry, vol. 3, p. 1423–1435 (2003).*
Navari, et al., *New England J. of Medicine*, vol. 340,pp. 190–195 (1999).
Maggi et al., *J. Auton. Pharmacol.*, vol. 13, pp. 23–93 (1993).
Kramer et al., *Science*, vol. 281, pp. 1640–1645 (1998).
Longmore et al., *Can. J. Physiol. Pharmacol.*, vol. 75, pp. 612–621 (1997).
Barker, *Reviews in Neurosciences*, vol. 7, pp. 187–214 (1996).
Maggi et al., *Neuropeptides.*, vol. 32(1), pp. 1–49 (1998).
Doi et al., *Eur. J. of Pharmacology.*, vol. 383(3), pp. 297–303 (1999).
Palma et al., *Life Sciences.*, vol. 67(9), pp. 985–1001 (2000).
Mutra et al., *Nature.*, vol. 405, pp. 180–183 (2000).

* cited by examiner

*Primary Examiner*—Richard L. Raymond
*Assistant Examiner*—Zachary C. Tucker
(74) *Attorney, Agent, or Firm*—George W. Johnston; Patricia S. Rocha-Tramaloni; Kimberly J. Prior

(57) ABSTRACT

The invention is the compounds
2-(3,5-bis-trifluoromethyl-phenyl)-N-[6-(1,1-dioxo-1$\lambda^6$-thiomorpholin-4-yl)-4-o-tolyl-pyridin-3-yl]-N-methyl-isobutyramide and
2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide.
Compounds of the invention are useful in pharmaceutical compositions for the treatment of migraine, rheumatoid arthritis, asthma, bronchial hyperreactivity, inflammatory bowel disease or for the treatment of disorders including Parkinson's disease, anxiety, depression, pain, headache, Alzheimer's disease, multiple sclerosis, edema, allergic rhinitis, Crohn's disease, ocular injury, ocular inflammatory diseases, psychosis, motion sickness, induced vomiting, emesis, urinary incontinence, psychoimmunologic or psychosomatic disorders, cancer, withdrawal symptoms of addictive drugs from opiates or nicotine, traumatic brain injury or benign prostatic hyperplasia.

9 Claims, No Drawings

AROMATIC AND HETEROAROMATIC SUBSTITUTED AMIDES

FIELD OF INVENTION

The invention relates to a compound of formula

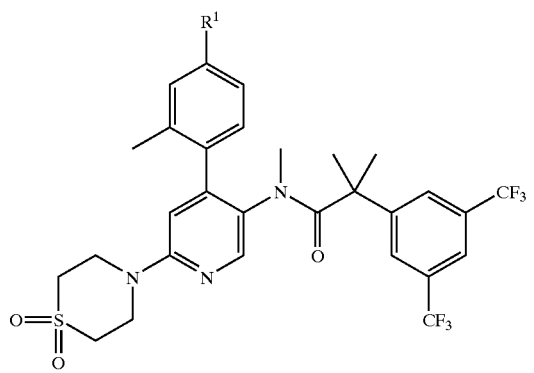

I wherein
R$^1$ is selected from the group consisting of hydrogen and fluoro. Compounds of formula 1, and pharmaceutically acceptable acid addition salts thereof, have been shown to mediate the Neurokinin 1 (NK-1, substance P) receptor.

BACKGROUND

The neuropeptide receptor for substance P (NK-1) is widely distributed throughout the mammalian nervous system (especially brain and spinal ganglia), the circulatory system and peripheral tissues (especially the duodenum and jejunum) and are involved in regulating a number of diverse biological processes. The receptor for substance P is a member of the superfamily of G protein-coupled receptors.

The central and peripheral actions of the mammalian tachykinin substance P have been associated with numerous inflammatory conditions including migraine, rheumatoid arthritis, asthma, and inflammatory bowel disease as well as mediation of the emetic reflex and the modulation of central nervous system (CNS) disorders such as Parkinson's disease (Neurosci. Res., 1996, 7, 187–214), anxiety (Can. J. Phys., 1997, 75, 612–621) and depression (Science, 1998, 281, 1640–1645).

Evidence for the usefulness of tachykinin receptor antagonists in pain, headache, especially migraine, Alzheimer's disease, multiple sclerosis, attenuation of morphine withdrawal, cardiovascular changes, edema, such as edema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases has been reviewed in "Tachykinin Receptor and Tachykinin Receptor Antagonists", J. Auton. Pharmacol., 13, 23–93, 1993.

Furthermore, Neurokinin 1 receptor antagonists are being developed for the treatment of a number of physiological disorders associated with an excess or imbalance of tachykinin, in particular substance P. Examples of conditions in which substance P has been implicated include disorders of the central nervous system such as anxiety, depression and psychosis (WO 95/16679, WO 95/18124 and WO 95/23798).

The neurokinin-1 receptor antagonists are further useful for the treatment of motion sickness and for treatment induced vomiting.

In addition, in The New England Journal of Medicine, Vol. 340, No. 3, 190 . 195, 1999 has been described the reduction of cisplatin-induced emesis by a selective neurokinin-1-receptor antagonist.

The usefulness of neurokinin 1 receptor antagonists for the treatment of certain forms of urinary incontinence is further described in Neuropeptides, 32(1), 1–49, (1998) and Eur. J. Pharmacol., 383(3), 297–303, (1999).

Furthermore, U.S. Pat. No. 5,972,938 describes a method for treating a psychoimmunologic or a psychosomatic disorder by administration of a tachykinin receptor, such as NK-1 receptor antagonist.

Life Sci., (2000), 67(9), 985–1001 describes, that astrocytes express functional receptors to numerous neurotransmitters including substance P, which is an important stimulus for reactive astrocytes in CNS development, infection and injury. In brain tumors malignant glial cells originating from astrocytes are triggered by tachykinins via NK-1 receptors to release soluble mediators and to increase their proliferative rate. Therefore, selective NK-1 receptor antagonists maybe useful as a therapeutic approach to treat malignant gliomas in the treatment of cancer.

In Nature (London) (2000), 405(6783), 180–183 is described that mice with a genetic disruption of NK-1 receptor show a loss of the rewarding properties of morphine. Consequently NK-1 receptor antagonists may be useful in the treatment of withdrawal symptoms of addictive drugs such as opiates and nicotine and reduction of their abuse/craving.

NK1 receptor antagonists have been reported to have also a beneficial effect in the therapy of traumatic brain injury (oral disclosure by Prof. Nimmo at the International Tachykinin Conference 2000 in La Grande Motte, France, Oct. 17–20, 2000 with the title "Neurokinin 1 (NK-1) Receptor Antagonists Improve the Neurological Outcome Following Traumatic Brain Injury" (Authors: A. J. Nimmo, C. J. Bennett, X.Hu, I. Cernak, R. Vink).

Aromatic and heteroaromatic substituted amides are generically described in EP 1035115.

SUMMARY

The present invention is directed to a compound of formula

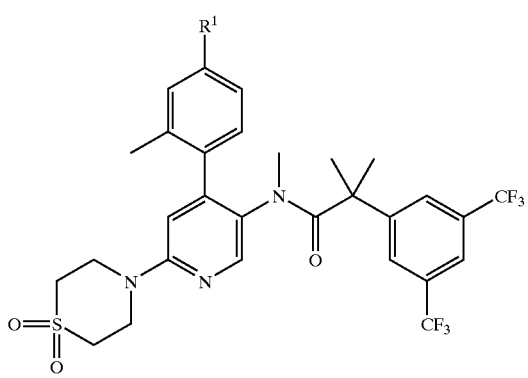

I or a pharmaceutically acceptable salt thereof, wherein R$^1$ is selected from the group consisting of hydrogen and fluoro.

The compounds of the present invention are further useful for the treatment of benign prostatic hyperplasia (BPH), which is common in older men. BPH can be progressive and lead to urinary retention, infections, bladder calculi and renal failure. This indication has been reported in EP 01109853.0.

The compounds of formula I can also be used in the form of their prodrugs, for example in form of their N-oxides. The prodrugs may add to the value of the present compounds advantages in adsorption, pharmacokinetics in distribution and transport to the brain.

DETAILED DESCRIPTION

Preferred compounds of formula I of the invention are:
2-(3,5-bis-trifluoromethyl-phenyl)-N-[6-(1,1-dioxo-1λ⁶-thiomorpholin-4-yl)-4-o-tolyl-pyridin-3-yl]-N-methyl-isobutyramide and
2-(3,5-bis-trifluoromethyl-phenyl)-N-[6-(1,1-dioxo-1λ⁶-thiomorpholin-4-yl)-4-(4-fluoro-2-methyl-phenyl)-pyridin-3-yl]-N-methyl-isobutyramide.

The compounds of formula I and their pharmaceutically acceptable salts are characterized by valuable therapeutic properties. It has been found that the compounds of the present invention are highly selective antagonists of the Neurokinin 1 (NK-1, substance P) receptor. Substance P is a naturally occurring undecapeptide belonging to the tachykinin family of peptides, the latter being so-named because of their prompt contractile action on extravascular smooth muscle tissue.

A method of treatment for benign prostatic hyperplasia (BPH), which is common in older men comprises administering a therapeutically effective amount of a compound of formula I, or a pharmaceutically acceptable salt thereof to a person in need of such treatment BPH can be progressive and lead to urinary retention, infections, bladder calculi and renal failure. This indication has been reported in EP 01109853.0.

The compounds of formula I can also be used in the form of their prodrugs, for example in form of their N-oxides. The prodrugs may add to the value of the present compounds advantages in adsorption, pharmacokinetics in distribution and transport to the brain.

An object of the present invention is a compound of formula I or a pharmaceutically acceptable salt thereof. Other objects of the present invention are the preparation of a compound of formula I, a pharmaceutical composition containing a therapeutically effective amount of a compound of formula I or a pharmaceutically acceptable salt thereof and preparation of the pharmaceutical composition. Yet another object of the present invention is a method of treatment, control or prevention of illnesses responsive to an antagonist of the Neurokinin 1 (NK-1, substance P) receptor comprising administering a therapeutically effective amount of a compound of formula I, or a pharmaceutically acceptable salt thereof, to a person in need of such treatment.

The preferred method of treatment of the present invention, is for disorders of the central nervous system, for example the treatment or prevention of certain depressive disorders, anxiety or emesis by the administration of the NK-1 receptor antagonist of the invention. A major depressive episode has been defined as being a period of at least two weeks during which, for most of the day and nearly every day, there is either depressed mood or the loss of interest or pleasure in all, or nearly all activities.

As described herein, the term "pharmaceutically acceptable acid addition salts" embraces salts with pharmaceutically acceptable inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

The present compounds of formula I and their pharmaceutically acceptable salts can be prepared by methods known in the art, for example, by a process described below, comprising reacting the compound of formula

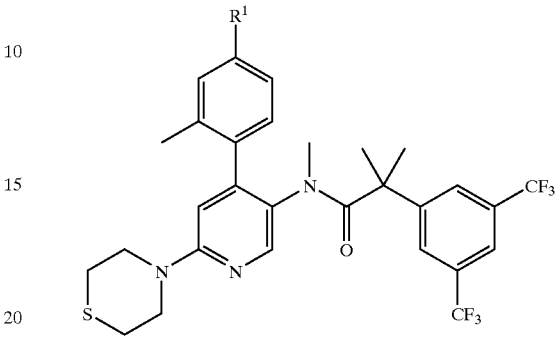

with OXONE® (potassium peroxymonosulfate, available from E.I.duPont, Wilmington, Del.)
thereby forming the compound of formula

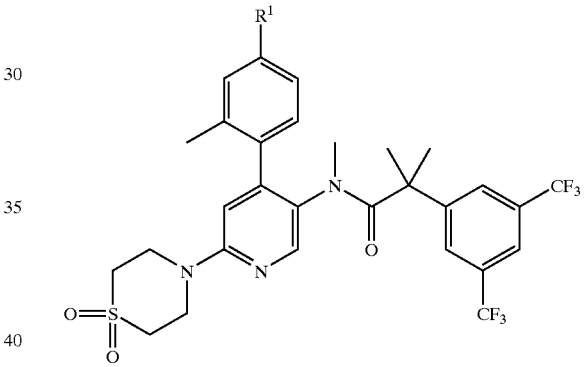

wherein R¹ is selected from the group consisting of hydrogen or fluoro, and, if desired, converting the compound obtained into a pharmaceutically acceptable acid addition salt.

In accordance with the process variant described above, to a solution of 2-(3,5-bis-trifluoromethyl-phenyl)-N-methyl-N-(6-thiomorpholin-4-yl-4-o-tolyl-pyridin-3-yl-)-isobutyramide or 2-(3,5-bis-trifluoromethyl-phenyl)-N-methyl-N-(6-thiomorpholin-4-yl-4-(4-fluoro-2-methyl-phenyl)-pyridin-3-yl)-isobutyramide in an alcohol, such as methanol, is added OXONE® or other suitable oxidation reagent known to a person skilled in the art, and the mixture is stirred at room temperatures for about two days. The desired compound of formula I is yielded after purification in good yields.

The salt formation is effected at room temperature in accordance with methods which are known to a person skilled in the art. Not only salts with inorganic acids, but also salts with organic acids are possible. Hydrochlorides, hydrobromides, sulfates, nitrates, citrates, acetates, maleates, succinates, methanesulfonates, p-toluenesulfonates and the like are examples of such salts.

The following scheme and examples 1 and 2 describe the processes for the preparation of the compounds of formula I in more detail. The starting materials of formulae III, IV, VIII and XII are known compounds or may be prepared according to methods known in the art.

In the schemes the following abbreviations have been used:
PivCl pivaloyl chloride
THF tetrahydrofuran
TMED N,N,N',N'-tetramethylethylene diamine
DIPEA N-ethyldiisopropyl-amine
TMP 2,2,6,6-tetramethylpiperidine
OXONE® potassium peroxymonosulfate $(2KHSO_5 \cdot KHSO_4 \cdot K_2SO_4)$ Scheme

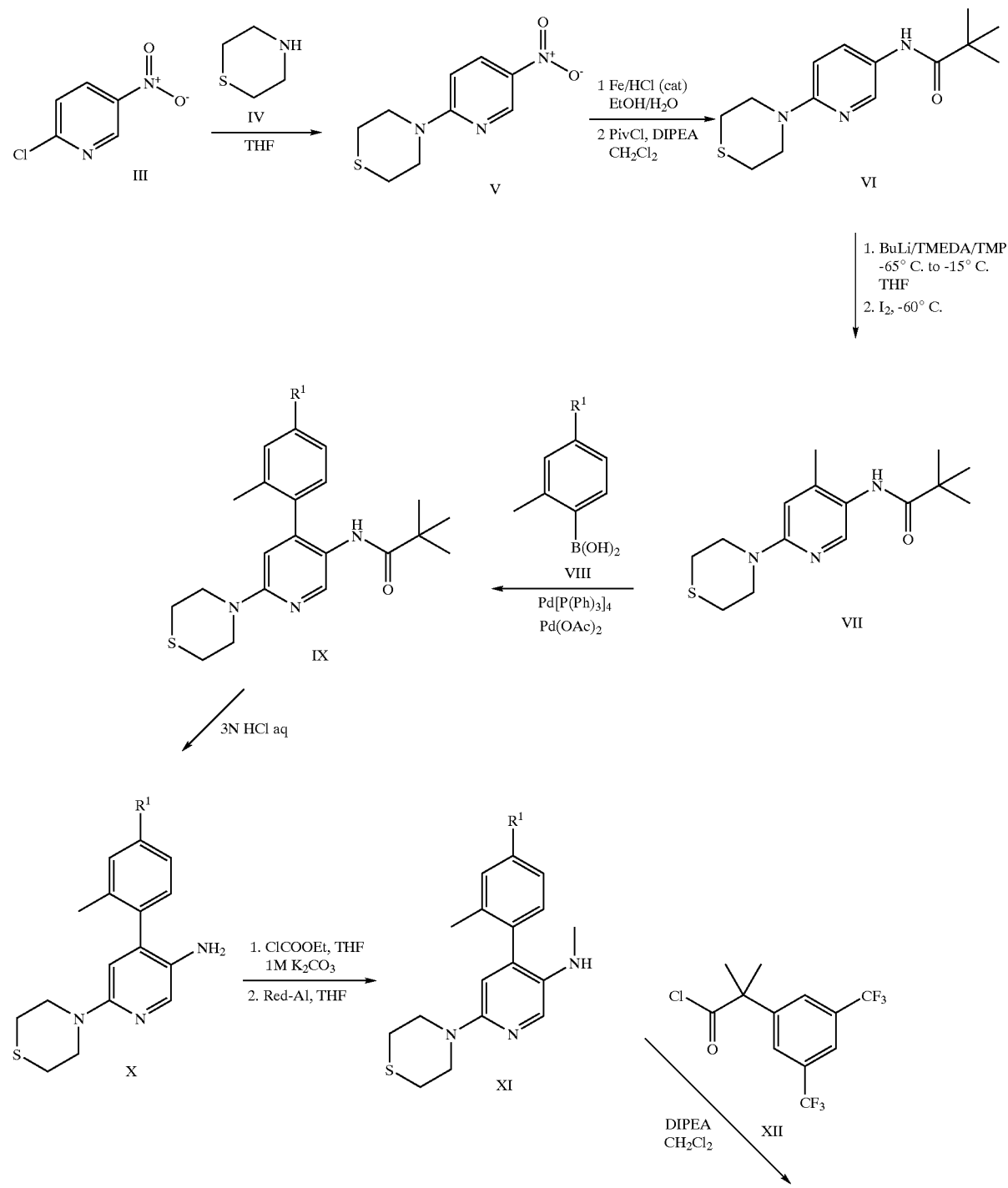

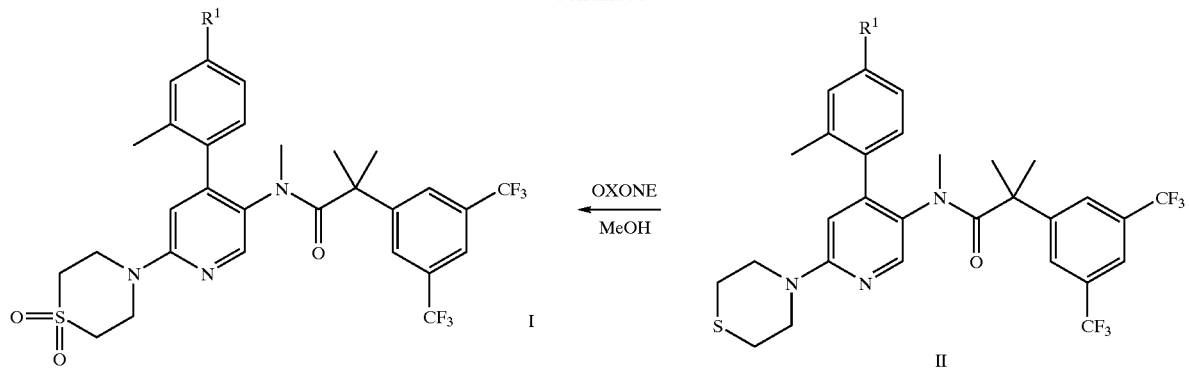

In this scheme R[1] is hydrogen or fluoro.

As mentioned earlier, the compounds of formula I and their pharmaceutically usable addition salts possess valuable pharmacological properties. It has been found that the compounds of the present invention are antagonists of the Neurokinin 1 (NK-1, substance P) receptor.

The compounds of formula I were investigated in accordance with the tests given hereinafter.

The affinities of the compounds 2-(3,5-bis-trifluoromethyl-phenyl)-N-[6-(1,1-dioxo-1λ[6]-thiomorpholin-4-yl)-4-o-tolyl-pyridin-3-yl]-N-methyl-isobutyramide and 2-(3,5-bis-trifluoromethyl-phenyl)-N-[6-(1,1-dioxo-1λ[6]-thiomorpholin-4-yl)-4-(4-fluoro-2-methyl-phenyl)-pyridin-3-yl]-N-methyl-isobutyramide for the human NK$_1$ receptor were evaluated in Chinese Hamster Ovary (CHO) cells transfected with the human NK$_1$ receptor (using the Semliki Virus expression system) and radiolabelled with [3H]substance P (final concentration 0.6 nM). Binding assays were performed in HEPES buffer (50 mM, pH 7.4) containing BSA (0.04%), leupeptin (8 μg/ml), MnCl$_2$ (3 mM) and phosphoramidon (2 μM). Binding assays consisted of 250 μl of membrane suspension (1.25×10[5] cells/assay tube), 0.125 μl of buffer of displacing agent and 125 μl of [3H] substance P. Displacement curves were determined with at least seven concentrations of the compound. The assay tubes were incubated for 60 min at room temperature after which time the tube contents were rapidly filtered under vacuum through GF/C filters presoaked for 60 min with PEI (0.3%) with 2×2 ml washes of HEPES buffer (50 mM, pH 7.4). The radioactivity retained on the filters was measured by scintillation counting. All assays were performed in triplicate in at least 2 separate experiments.

The compounds 2-(3,5-bis-trifluoromethyl-phenyl)-N-[6-(1,1-dioxo-1λ[6]-thiomorpholin-4-yl)-4-o-tolyl-pyridin-3-yl]-N-methyl-isobutyramide and 2-(3,5-bis-trifluoromethyl-phenyl)-N-[6-(1,1-dioxo-1λ[6]-thiomorpholin-4-yl)-4-(4-fluoro-2-methyl-phenyl)-pyridin-3-yl]-N-methyl-isobutyramide are potent and selective ligands for recombinant human NK$_1$ receptors expressed in CHO cells. They have affinities (pKi) of 8.9 and 9.5 for the human NK$_1$ receptor, respectively and over 3 orders of magnitude of selectivity for the NK$_1$ receptor compared to other neurokinin receptors.

The activity in vitro was examined by studying its effect on substance P induced Ca$^{2+}$ influxes in CHO cells expressing the recombinant human NK$_1$ receptor. In these cells, substance P causes a concentration dependent influx of Ca$^{2+}$ which can be measured using FLIPR technology. Increasing concentrations of either 2-(3,5-bis-trifluoromethyl-phenyl)-N-[6-(1,1-dioxo-1λ[6]-thiomorpholin-4-yl)-4-o-tolyl-pyridin-3-yl]-N-methyl-isobutyramide or 2-(3,5-bis-trifluoromethyl-phenyl)-N-[6-(1,1-dioxo-1λ[6]-thiomorpholin-4-yl)-4-(4-fluoro-2-methyl-phenyl)-pyridin-3-yl]-N-methyl-isobutyramide inhibited the substance P induced Ca$^{2+}$ influx. These data indicate that both compounds are antagonists at human NK$_1$ receptors.

In vivo 2-(3,5-bis-trifluoromethyl-phenyl)-N-[6-(1,1-dioxo-1λ[6]-thiomorpholin-4-yl)-4-o-tolyl-pyridin-3-yl]-N-methyl-isobutyramide antagonizes foot-tapping behavior induced in Gerbils with intracerebroventricular (i.c.v.) injections of an NK$_1$ receptor agonist. The dose for this compound calculated to inhibit 50% of the foot-tapping behavior following oral administration was 0.8 mg/kg. The plasma levels required to completely antagonize this behavior have also been measured and it was found that a total plasma concentration of 10 ng/ml is required to completely block the foot-tapping behavior. Similarly, 2-(3,5-bis-trifluoromethyl-phenyl)-N-[6-(1,1-dioxo-1λ[6]-thiomorpholin-4-yl)-4-(4-fluoro-2-methyl-phenyl)-pyridin-3-yl]-N-methyl-isobutyramide also antagonized NK$_1$ agonist-induced foot-tapping in Gerbils. The dose for this compound calculated to inhibit 50% of the foot-tapping behavior following oral administration was 0.1 mg/kg. The total plasma levels that are required to completely antagonize this behavior are less than 10 ng/ml.

Therefore, in conclusion, both 2-(3,5-bis-trifluoromethyl-phenyl)-N-[6-(1,1-dioxo-1λ[6]-thiomorpholin-4-yl)-4-o-tolyl-pyridin-3-yl]-N-methyl-isobutyramide and 2-(3,5-bis-trifluoromethyl-phenyl)-N-[6-(1,1-dioxo-1λ[6]-thiomorpholin-4-yl)-4-(4-fluoro-2-methyl-phenyl)-pyridin-3-yl]-N-methyl-isobutyramide are potent antagonists of NK$_1$ induced behaviors in the Gerbil.

The pharmacokinetic parameters of both compounds have been evaluated in both rats and dogs. In rats, 2-(3,5-bis-trifluoromethyl-phenyl)-N-[6-(1,1-dioxo-1λ[6]-thiomorpholin-4-yl)-4-o-tolyl-pyridin-3-yl]-N-methyl-isobutyramide has a terminal half-life of 9 hours, a clearance of 4.7 ml/min/kg, a volume of distribution of 4 l/kg and an oral bioavailability of 18%. In dogs the molecule had a half-life of 8 hours, a clearance of 5 ml/min/kg and a volume of distribution of 4 l/kg. Similarly, in rats 2-(3,5-bis-trifluoromethyl-phenyl)-N-[6-(1,1-dioxo-1λ[6]-thiomorpholin-4-yl)-4-(4-fluoro-2-methyl-phenyl)-pyridin-3-yl]-N-methyl-isobutyramide has a terminal half-life of 21 hours, a clearance of 0.3–1.2 ml/min/kg, a volume of distribution of 0.7 l/kg and an oral bioavailability of 61%. In dogs the molecule had a half-life of 56 hours, a clearance of 1.4 ml/min/kg and a volume of distribution of 1.5 l/kg.

The compounds of formula I as well as their pharmaceutically usable acid addition salts can be used in the form of pharmaceutical compositions. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and their pharmaceutically usable acid addition salts can be processed with pharmaceutically inert, inorganic or organic excipients for the production of tablets, coated tablets, dragees and hard gelatin capsules. Lactose, corn starch or derivatives thereof, talc, stearic acid or its salts etc. can be used as such excipients e.g. for tablets, dragées and hard gelatin capsules.

Suitable excipients for soft gelatin capsules are e.g. vegetable oils, waxes, fats, semi-solid and liquid polyols etc.

Suitable excipients for the manufacture of solutions and syrups are e.g. water, polyols, saccharose, invert sugar, glucose etc.

Suitable excipients for injection solutions are e.g. water, alcohols, polyols, glycerol, vegetable oils etc.

Suitable excipients for suppositories are e.g. natural or hardened oils, waxes, fats, semi-liquid or liquid polyols etc.

Moreover, the pharmaceutical preparations can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary within wide limits and will, of course, be fitted to the individual requirements in each particular case. In general, in the case of oral administration a daily dosage of about 10 to 1000 mg per person of the compound of formula I should be appropriate, although the above upper limit can also be exceeded when necessary.

The following Examples 1 and 2 illustrate the present invention without limiting it. All temperatures are given in degrees Celsius.

EXAMPLE 1

2-(3,5-Bis-trifluoromethyl-phenyl)-N-[6-(1,1-dioxo-1$\lambda^6$-thiomorpholin-4-yl)-4-o-tolyl-pyridin-3-yl]-N-methyl-isobutyramide a) 4-(5-Nitro-pyridin-2-yl)-thiomorpholine To a solution of 20 g (126 mmol) of 2-chloro-5-nitropyridine in 200 ml tetrahydrofuran were added dropwise 32.5 ml (315 mmol) thiomorpholine within 10 min. The reaction mixture was refluxed for additional 2 h. After cooling to room temperature, the solvent was removed in vacuo and the residue was re-dissolved in 200 ml ethyl acetate. The organic phase was washed with 200 ml 1 N sodium bicarbonate solution, dried (magnesium sulfate) and evaporated to give 29.3 g (quantitative) of the title compound as a yellow solid.

MS m/e (%): 225 (M$^+$, 78), 152 (100), 124 (62).

b) 2,2-Dimethyl-N-(6-thiomorpholin-4-yl-pyridin-3-yl)-propionamide

To a suspension of 1.0 g (4.4 mmol) of 4-(5-nitro-2-pyridyl)-thiomorpholine in 8 ml ethanol and 2 ml water were added 1.5 g (27 mmol) of iron powder. A few drops of 3 N hydrochloric acid solution in diethyl ether were added and the reaction mixture was heated at 85° C. for 18 h. The suspension was filtered and the residue was washed 5 times with 10-ml portions of ethanol. The filtrate was evaporated in vacuo to give 870 mg of a purple oil. This crude product was dissolved in 10 ml dichloromethane. Under stirring, 700 mg (6 mmol) of pivaloyl chloride and 860 mg (7 mmol) of N-ethyldiisopropyl-amine were added and the reaction mixture was stirred at room temperature overnight. Then, 30 ml water and 3 ml of 1 N hydrochloric acid solution were added to reach pH 1. The organic layer was separated and the aqueous layer was washed with 1 N hydrochloric acid solution, adjusted to pH 10 with sodium carbonate and extracted with dichloromethane. The organic layer was dried (sodium sulfate) and evaporated to give 630 mg (51%) of the title compound as purple crystals.

MS m/e (%): 280 (M+H$^+$, 100).

c) N-(4-Iodo-6-thiomorpholin-4-yl-pyridin-3-yl)-2,2-dimethyl-propionamide

Under argon) a solution of 75 g (268 mmol) 2,2-dimethyl-N-(6-thiomorpholin-4-yl-pyridin-3-yl)-propionamide, 187 g (1.61 mol) N,N,N',N'-tetramethylethylenediamine and 85 g (604 mmol) 2,2,6,6,-tetramethylpiperidine in 750 ml tetrahydrofuran was cooled to −65° C. in a dry ice bath. Within 30 min, 805 ml (1.29 mol) of a 1.6 N n-butyllithium solution in hexane were added dropwise. The reaction mixture was allowed to warm up to −15° C. and was stirred for 3 h at this temperature. After cooling again to −70° C., 354 g (1.40 mol) iodine (dissolved in 1000 ml tetrahydrofuran) were added dropwise during 2 h and stirring was continued for 1 h. The suspension was warmed to −60° C. and was poured into 1000 ml of 30% sodium thiosulfate pentahydrate solution. Then, 750 ml tert-butyl methyl ether were added and the organic layer was separated. The aqueous layer was extracted three times with 750-ml portions of tert-butyl methyl ether and the combined organic layers were dried (sodium sulfate) and evaporated. Flash chromatography gave 68.9 g (63%) of the title compound as light brown crystals.

MS m/e (%): 406 (M+H$^+$, 100).

d) 2,2-Dimethyl-N-(6-thiomorpholin-4-yl-4-o-tolyl-pyridin-3-yl)-propionamide

A mixture of 4.05 g (10.0 mmol) N-(4-iodo-6-thiomorpholin-4-yl-pyridin-3-yl)-2,2-dimethyl-propionamide, 54 ml toluene, 16 ml 2 N sodium carbonate solution, 347 mg (0.3 mmol) tetrakis(triphenylphosphine) palladium(0), 67 mg (0.3 mmol) palladium(II) acetate and 1.50 g (11.0 mmol) o-tolylboronic acid was heated under argon at 80° C. for 18 h. After cooling to room temperature, the aqueous phase was separated and washed twice with ethyl acetate. The combined organic layers were washed with 50 ml brine, dried (sodium sulfate) and evaporated. Purification by flash-chromatography gave 3.57 g (quantitative) of the title compound as a light brown solid.

MS m/e (%): 392 (M+Na$^+$, 4), 370 (M+H$^+$, 100).

e) 6-Thiomorpholin-4-yl-4-o-tolyl-pyridin-3-ylamine

A suspension of 3.45 g (9.3 mmol) 2,2-dimethyl-N-(6-thiomorpholin-4-yl-4-o-tolyl-pyridin-3-yl)-propionamide in 95 ml 3 N hydrochloric acid solution was heated under argon at 110° C. overnight. The reaction mixture was cooled to room temperature, washed with two 100-ml portions of diethyl ether and filtered over celite. The filtrate was diluted with 20 ml water and was adjusted to pH 11 by addition of 28% sodium hydroxide solution under ice cooling. The product was extracted with three 100-ml portions of dichloromethane. The combined organic layers were washed with 50 ml brine, dried (sodium sulfate) and evaporated to give 2.53 g (95%) of the title compound as a brown solid.

MS m/e (%):286 (M+H$^+$, 100).

f) Methyl-(6-thiomorpholin-4-yl-4-o-tolyl-pyridin-3-yl)-amine

To a solution of 2.46 g (8.6 mmol) 6-thiomorpholin-4-yl-4-o-tolyl-pyridin-3-ylamine in 38 ml tetrahydrofuran were added 2.38 g (17 mmol) potassium carbonate (dissolved in 25 ml water) and 1.03 g (9.5 mmol) ethyl cloroformate. The reaction mixture was stirred for 1 h at room temperature and evaporated to remove tetrahydrofuran. The aqueous layer was extracted twice with 50-ml portions of dichloromethane and the organic layer was dried (sodium sulfate) and evaporated in vacuo. The residual oil was dissolved in 30 ml tetrahydrofuran and 7.4 ml (2.6 mmol) 3.5 M sodium bis(2-methoxyethoxy)aluminum hydride solution in toluene were added within 30 min. The reaction mixture was stirred at 50° C. overnight. After cooling to 0° C., 7.5 ml 1 N sodium hydroxide solution were added dropwise. Tetrahydrofuran was removed in vacuo and 10 ml of water were added. The aqueous layer was extracted twice with 20-ml portions of dichloromethane and the combined organic layers were dried (sodium sulfate), evaporated and purified by flash chromatography to give 2.37 g (92%) of the title compound as a yellow solid.

MS m/e (%): 300 (M+H$^+$, 100).

g) 2-(3,5-Bis-trifluoromethyl-phenyl)-N-methyl-N-(6-thiomorpholin-4-yl-4-o-tolyl-pyridin-3-yl)-isobutyramide A solution of 2.32 g (7.7 mmol) methyl-(6-thiomorpholin-4-yl-4-o-tolyl-pyridin-3-yl)-amine and 1.50 g (11.6 mmol) N-ethyldiisopropylamine in 20 ml tetrahydrofuran was cooled in an ice bath and 2.72 g (8.5 mmol) 2-(3,5-bis-trifluoromethyl-phenyl)-2-methyl-propionyl chloride were added dropwise. The reaction mixture was stirred at room temperature overnight and evaporated in vacuo. The residue was suspended in 200 ml 1 N sodium carbonate solution and extracted three times with 200-ml portions of ethyl acetate. The combined organic layers were dried (sodium sulfate) and evaporated. The residue was crystallized from ethanol to give 3.60 g (80%) of the title compound as white crystals.

MS m/e (%): 582 (M+H$^+$, 100).

h) 2-(3,5-Bis-trifluoromethyl-phenyl)-N-[6-(1,1-dioxo-1$\lambda^6$-thiomorpholin-4-yl)-4-o-tolyl-pyridin-3-yl]-N-methyl-isobutyramide To a solution of 1.00 g (1.72 mmol) 2-(3,5-bis-trifluoromethyl-phenyl)-N-methyl-N-(6-thiomorpholin-4-yl-4-o-tolyl-pyridin-3-yl)-isobutyramide in 10 ml methanol were added 1.59 g (2.58 mmol) OXONE®. After stirring for 2 days at room temperature, 5 ml 38% sodium hydrogensulfite solution and 20 ml saturated sodium carbonate solution were added consecutively and methanol was removed in vacuo. The residue was diluted with 25 ml water and extracted with three 25-ml portions of dichloromethane. The combined organic layers were dried (sodium sulfate), purified by flash chromatography and crystallized from ethanol to give 980 mg (93%) of the title compound as white crystals. M.p. 200–201° C.

MS m/e (%): 636 (M+Na$^+$, 20), 614 (M+H$^+$, 100).

EXAMPLE 2

2-(3,5-Bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide The title compound was obtained as white crystals in comparable yields according to the procedures described above for the preparation of 2-(3,5-bis-trifluoromethyl-phenyl)-N-[6-(1,1-dioxo-1$\lambda^6$-thiomorpholin-4-yl)-4-o-tolyl-pyridin-3-yl]-N-methyl-isobutyramide using 4-fluoro-2-methyl-phenylboronic acid instead of o-tolylboronic acid in step d). M.p. 162.1–163.6° C.

EXAMPLE A

Tables of the following composition are manufactured in the usual manner:

|  | mg/tablet |
|---|---|
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
|---|---|
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatin capsules.

EXAMPLE C

Suppositories of the following composition are manufactured:

|  | mg/supp. |
|---|---|
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository molds of suitable size, left to cool, the suppositories are then removed from the molds and packed individually in wax paper or metal foil.

EXAMPLE D

An injection solution may have the following composition and is manufactured in usual manner:

| Active substance | 1.0 mg |
|---|---|
| 1 n HCl | 20.0 µl |
| acetic acid | 0.5 mg |
| NaCl | 8.0 mg |
| phenol | 10.0 mg |
| 1 n NaOH | q.s. ad pH 5 |
| H$_2$O | q.s. ad 1 ml |

What is claimed is:

1. A compound of formula

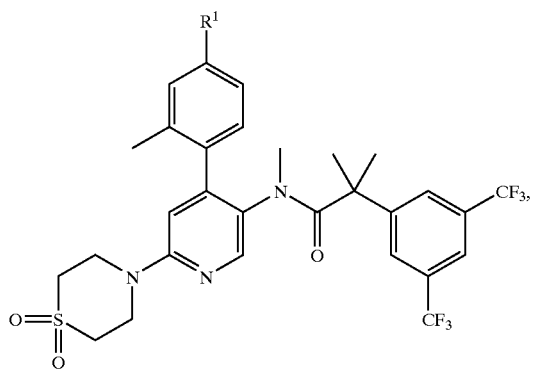

wherein $R^1$ is selected from the group consisting of hydrogen and fluoro, or a pharmaceutically acceptable salt thereof.

2. A compound, 2-(3,5-bis-trifluoromethyl-phenyl)-N-[6-(1,1-dioxo-1$\lambda^6$-thiomorpholin-4-yl)-4-o-tolyl-pyridin-3-yl]-N-methyl-isobutyramide.

3. A compound, 2-(3,5-bis-trifluoromethyl-phenyl)-N-[6-(1,1-dioxo-1$\lambda^6$-thiomorpholin-4-yl)-4-(4-fluoro-2-methyl-phenyl)-pyridin-3-yl]-N-methyl-isobutyramide.

4. A pharmaceutical composition containing at least one compound of formula I, or a pharmaceutically acceptable salt thereof and at least one pharmaceutically acceptable excipient.

5. A method of treatment of depressive disorders, anxiety or emesis comprising administering to an individual a therapeutically effective amount of a compound of formula 1, or a pharmaceutically acceptable salt thereof, according to claim 1.

6. A method of treatment of anxiety comprising administering to an individual a therapeutically effective amount of a compound of formula I, or a pharmaceutically acceptable salt thereof.

7. A method of treatment of emesis comprising administering to an individual a therapeutically effective amount of a compound of formula I, or a pharmaceutically acceptable salt thereof.

8. A process for preparing a compound of formula I comprising
reacting a compound of formula

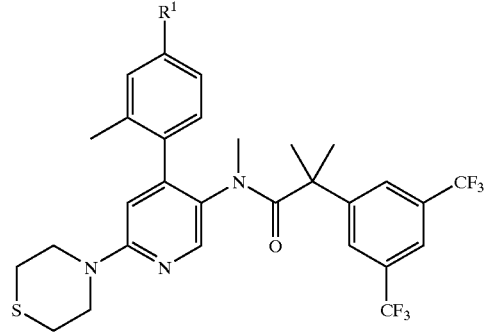

with potassium peroxymonosulfate
forming a compound of formula

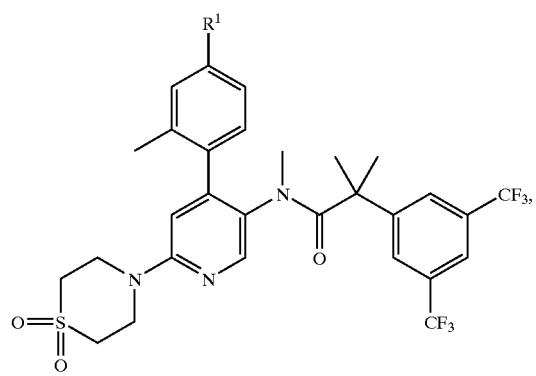

wherein $R^1$ is selected from the group consisting of hydrogen and fluoro.

9. A method of treatment of depressive disorders comprising administering to an individual a therapeutically effective amount of a compound of formula I, or a pharmaceutically acceptable salt thereof.

* * * * *